United States Patent [19]

Nishikido et al.

[11] 4,256,645

[45] Mar. 17, 1981

[54] PROCESS FOR PRODUCING GLUCONA-DELTA-LACTONE FROM GLUCOSE

[75] Inventors: Joji Nishikido; Nobuhiro Tamura; Yohei Fukuoka, all of Fuji, Japan

[73] Assignee: Asahi Kasei Kogyo Kabushiki Kaisha, Osaka, Japan

[21] Appl. No.: 75,457

[22] Filed: Sep. 14, 1979

[30] Foreign Application Priority Data

Sep. 14, 1978 [JP] Japan ............................... 53/112361
Oct. 2, 1978 [JP] Japan ............................... 53/120397
Nov. 17, 1978 [JP] Japan ............................... 53/141215
Jan. 16, 1979 [JP] Japan ............................... 54/2281

[51] Int. Cl.$^3$ .......................................... C07D 309/30
[52] U.S. Cl. ................................................. 260/343.5
[58] Field of Search ..................................... 260/343.5

[56] References Cited

U.S. PATENT DOCUMENTS 2,102,380  12/1937  Pasternack .................. 260/343.5
2,491,452  12/1949  Kern et al. .................. 260/343.5

OTHER PUBLICATIONS

Acres et al., Chem. Abst., vol. 74, 1971, 14347h.
Kiyoura et al., Chem. Abst., 85:160467r.
Hattori et al., Chem. Abst., 89:110271j.
Kimura et al., Chem. Abst. 85:193032y.
de Wilt, Ind. Eng. Chem. Prod. Res. Develop., vol. 11, No. 4, 1972, pp. 370–373, TP1I532.
Green, The Carbohydrates, edited by Pigman, 1957, pp. 299–301.

*Primary Examiner*—Henry R. Jiles
*Assistant Examiner*—Jane T. Fan
*Attorney, Agent, or Firm*—Sughrue, Rothwell, Mion, Zinn and Macpeak

[57] ABSTRACT

A process for producing glucono-delta-lactone from glucose by bringing glucose into contact with molecular oxygen in the presence of an organic solvent and a palladium or platinum catalyst. The process optionally includes an acid treatment.

18 Claims, No Drawings

PROCESS FOR PRODUCING GLUCONA-DELTA-LACTONE FROM GLUCOSE

BACKGROUND OF THE INVENTION

1. Field of the Invention

This invention relates to a process for producing glucono-delta-lactone from glucose and more particularly, to a process for producing glucono-delta-lactone by reacting glucose with molecular oxygen in the presence of an organic solvent using a palladium-containing catalyst for a platinum-containing catalyst.

2. Description of the Prior Art

Glucono-delta-lactone, sugar lactone certified for use as a food additive, has conventionally been used as a leavening agent for bread, cakes and other confections, and its use is expanding to encompass such products as bean curd, ham, sausage and boiled fish paste. Recently, demands are also increasing for glucono-delta-lactone in such fields as civil engineering, construction, and manufacture of medicines, cosmetics and detergents.

The conventional process for production of glucono-delta-lactone consists of preparing gluconic acid from glucose and converting the acid to lactone. Gluconic acid is prepared by several methods such as microbiological oxidation of glucose, electrolytic oxidation of glucose, and chemical oxidation of glucose with hypochlorous acid. Hence, glucono-delta-lactone has been produced by a two-step process that involves the step of converting glucose into gluconic acid.

SUMMARY OF THE INVENTION

Accordingly, a chief object of the present invention is to provide a one step process for producing glucono-delta-lactone.

Another object of the present invention is to provide a process for producing glucono-delta-lactone by chemical oxidation which provides high yields and selectivity and as a result is highly economical.

Another object of the present invention is to provide a process for producing glucono-delta-lactone which is suitable for commercial or large scale operations.

As the result of studies directed to an economical process for producing glucono-delta-lactone from glucose it has been found that glucono-delta-lactone can be produced in one step by reacting glucose with molecular oxygen in the presence of an organic solvent using a palladium or platinum catalyst. It has also been found that the yield and selectivity for the lactone is increased remarkably by using a palladium catalyst containing lead.

DETAILED DESCRIPTION OF THE INVENTION

The reaction occurring in the process of this invention allow glucono-delta-lactone to be produced in a single step as schematically shown below.

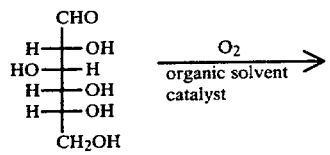

D-glucose

-continued

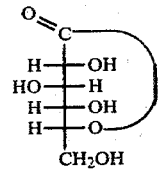

glucono-delta-lactone

It is surprising that the reaction for the production of delta-lactone proceeds with high selectivity in the oxidative reaction of a compound which, as shown above, contains primary and secondary free hydroxyl groups in the same molecule. Thus, the one step process of this invention is much more economical as compared with a conventional process and is advantageously employed in commercial production of glucono-delta-lactone.

The process of this invention features oxidation of glucose in the presence of an organic solvent that dissolves or disperses the glucose and a palladium or platinum catalyst.

A method is known to produce an alkali salt of gluconic acid from glucose by reacting glucose with molecular oxygen using a large amount of alkali and a palladium or platinum catalyst in an aqueous solvent. Unfortunately, the catalyst permits only a small amount of glucose to be converted to glucono-delta-lactone when the reaction of glucose is effected in an aqueous solvent. However, glucono-delta-lactone can be produced in one step using a palladium or platinum catalyst in an organic solvent with a high conversion ratio and selectivity. Particularly good results are obtained using a catalyst system of palladium and lead.

Only a very small amount of the catalyst is required to exhibit its effect and the reaction is completed in a short period of time and at low temperatures. Under the reaction conditions employed in the process of this invention, the catalyst suffers little loss in the activity and withstands extended use.

Any organic solvent may be used in this invention so long as it can dissolve or disperse glucose and will not deteriorate in the course of the reaction. Suitable examples are ethers, nitriles, alcohols, amides, esters, ketones, nitro compounds, pyridine bases, hydrocarbons and halogenated hydrocarbons. Exemplary ethers are diethyl ether, diisopropyl ether, dibutyl ether, phenylethyl ether, anisole, dimethoxyethane, diethylene glycol dimethyl ether, diethylene glycol diethyl ether, acetic ethylene glycol monomethyl ether, triethylene glycol dimethyl ether, ethylene glycol monoethyl ether, tetrahydrofuran, and dioxane. Exemplary nitriles are acetonitrile, propionitrile, n-butyronitrile, ethylene cyanohydrin, and benzonitrile. Exemplary alcohols are methanol, ethanol, propanol, n-butanol, and amyl alcohol. Exemplary amides are dimethylformamide, dimethylacetamide, N-methylpyrrolidone, tetramethylurea and hexamethyl phosphoryl amide. Exemplary esters are methyl formate, ethyl formate, methyl acetate, ethyl acetate, propyl acetate, butyl acetate, benzyl acetate, methyl acetoacetate, ethyl acetoacetate, and glycol diacetate. Exemplary ketones are acetone, methyl ethyl ketone, methyl propyl ketone, methyl butyl ketone, methyl isobutyl ketone and dipropyl ketone. Exemplary nitro compounds are nitromethane, nitroethane, trinitropropane, and nitrobenzene. Exemplary pyridine bases are pyridine, α-methylpyridine, β-methylpyridine and γ-methylpyridine. Exemplary hydrocarbons are n-pentane, n-hexane, heptane, cyclohexane, methylcyclohexane, benzene, toluene, xylene, ethylbenzene, diethylbenzene, and triethylbenzene. Exemplary halogenated hydrocarbons are chloroform, methylchloroform, 1,1,2-trichloroethane, 1,2,3-trichloroethane, trichloroethylene, ethylene chlorohydrin, ethylene dichloride, ethylene dibromide, chlorobenzene, dichlorobenzene and monochlorotoluene.

These solvents may be used independently or as a mixture. Water-miscible solvents may be used in combination with not greater than about 20 wt% of water. While these solvents may be used in an amount that varies depending on the type of catalyst, reaction temperature and reaction time, they are generally used in an amount 1 to 500 times, preferably from 10 to 200 times, greater than the glucose by weight. Preferred solvents are ethers, alcohols, amides, esters, acetonitrile, propionitrile, methyl ethyl ketone and the like, and of these dioxane, tetrahydrofuran, dimethoxyethane, diisopropyl ether, dibutyl ether, diethylene glycol dimethyl ether, triethylene glycol dimethyl ether, methanol, n-butanol, dimethylformamide, dimethylacetamide, tetramethylurea, methyl acetate and ethyl acetate are particularly preferred. Dioxane, tetrahydrofuran and dimethoxyethane are most preferred.

The catalyst used in this invention comprises metallic palladium or platinum. A palladium catalyst system containing lead permits the reaction to proceed with high yield and selectivity. Lead is preferably contained in the catalyst system at an atomic ratio to palladium of about 0.01 to 30, and an atomic ratio of about 0.1 to 10 is most suitable.

Lead may be added as metallic lead or a lead compound. The lead compound is a salt such as a halide, inorganic acid salt or organic acid salt or in the form of an oxide or hydroxide. Examples of the halide are the chloride, bromide, iodide and fluoride. Examples of the inorganic acid salt are salts of sulfuric acid, nitric acid, phosphoric acid and boric acid. Examples of the organic acid salt are salts of formic acid, acetic acid, propionic acid, stearic acid, malonic acid, succinic acid, glutaric acid, maleic acid, benzoic acid and phthalic acid.

While these catalysts may be unsupported, they are preferably borne on a carrier. Preferred carriers are those which are commonly used to carry noble metals such as activated carbon, silica, silica-alumina, alumina, calcium carbonate, calcium phosphate, barium sulfate and alumina-magnesia.

A platinum catalyst comprising a carrier impregnated with platinum is prepared by a conventional process which, for instance, consists of dissolving a platinum salt (e.g., chloroplatinic acid or an ammine complex salt of platinum chloride) in an aqueous solution, adsorbing the platinum salt on the carrier and reducing the adsorbed platinum salt with formalin, hydrazine or hydrogen. While platinum content on the carrier is not critical, it is generally in the range of from 0.1 to 20 wt%, preferably from about 1 to 10 wt%, based on the weight of the carrier.

A palladium catalyst comprising a carrier impregnated with palladium is prepared by a conventional process which, for instance, consists of mixing activated carbon with an aqueous solution of palladium chloride, stirring the mixture for several hours to have palladium chloride adsorbed on the carbon, and thereafter reducing palladium chloride with hydrogen, formalin or hydrazine. While palladium content on the carrier is not critical, it is generally in the range of from about 0.1 to 20 wt.%, preferably from about 1 to 10 wt%, based on the weight of the carrier.

A catalyst system containing palladium and a lead compound is prepared, for example, by mixing activated carbon with an aqueous solution of lead acetate, stirring the mixture for several hours such that the lead acetate is adsorbed on the carbon, calcining the carbon at 500° to 700° C., mixing the calcined carbon with an aqueous solution of palladium chloride under stirring for several hours to have palladium chloride adsorbed on the carbon, and thereafter reducing the chloride with formalin, hydrazine or hydrogen. While palladium content on the carrier is not critical, it is generally in the range of from about 0.1 to 20 wt%, preferably from 1 to 10 wt%, based on the weight of the carrier, regardless of the lead content.

A catalyst comprising metallic palladium and a hydroxide, inorganic acid salt, halide or organic acid salt of lead is prepared by first forming metallic palladium on a carrier as above, which is then mixed with an aqueous solution of a salt or hydroxide of lead under stirring such that the salt or hydroxide is adsorbed on the carrier. Alternatively, the lead compound may be introduced into the reaction system together with the metallic palladium catalyst.

While there is no particular limitation on the amount of platinum or palladium used in the reaction of this invention, a batch reaction requires about 0.001 to 1 atom and preferably about 0.01 to 0.5 atom of platinum or palladium per mol of glucose whether lead is used or not.

The molecular oxygen used in the process of this invention includes not only pure oxygen but also air which contains nitrogen and other inert gases. Oxygen should be present in the atmosphere used in an amount of at least 10% by volume.

The reaction can be performed under either atmospheric or superatmospheric pressure. The reaction temperature generally ranges from about 10° to 200° C., preferably from about 20° to 130° C. While the reaction time varies with the reaction temperature, the type of catalyst and its content, a reaction time of about 10 minutes to 7 hours, preferably from 30 minutes to 4 hours is used.

The process of this invention may be performed in a batch process or in a continuous process, with a palladium or platinum catalyst in powder or granular form, and using mixing means to provide adequate contact between gas and liquid on the catalyst surface.

As described hereinabove, according to this invention, glucono-delta-lactone is produced by oxidizing glucose using a palladium or platinum catalyst in the presence of an organic solvent which dissolves or disperses the glucose. However, a higher conversion ratio of glucose often causes the resulting glucono-delta-lactone to isomerize, which then reduces the selectivity for the lactone. It has been found that by treating the reaction mixture or the crude product with acid after the oxidative reaction, the isomerized lactone can be regenerated to the desired glucono-delta-lactone, thus leading to a higher yield and selectivity.

A preferred method of the acid treatment comprises, for instance, filtering off the catalyst after the reaction, transferring and treating the filtrate or, when the oxidative reaction is not performed in a solvent which is inert to the acid, the crude product from which the reaction solvent has been removed by distillation, to an inert solvent (i.e., a solvent which is non-reactive with the acid), and treating such with an acid. The inert solvent includes alcohols, ethers, esters and nitriles as defined for the organic solvent described above, and methanol, tetrahydrofuran, dioxane, dimethoxyethane, methyl acetate, ethyl acetate, acetonitrile and propionitrile are particularly preferred. The acid used herein includes an inorganic acid, organic acid, and an acidic ion exchange resin. Preferred inorganic acids are hydrochloric acid, sulfuric acid, nitric acid, phosphoric acid and boric acid. A preferred organic acid is an organic sulfonic acid, such as paratoluenesulfonic acid. The acidic ion exchange resin may be in a weak acid or strong acid form. A strong acidic ion exchange resin is preferred. Treatment with such acids is performed at a temperature in the range of from 10° to 70° C. Adequate results are obtained even if the range is from 20° to 40° C. An inorganic acid or organic acid used in an amount of from 0.001 to 0.1 mol, preferably from 0.005 to 0.1 mol, per mol of glucose is sufficient to achieve the intended result. The same amount of an ion exchange resin can also serve the purpose.

As described above, the process of this invention is a one step production of glucono-delta-lactone by oxidizing glucose in an organic solvent.

The process of this invention will hereunder be described in greater detail by reference to the following examples which are given here for illustrative purposes only and are by no means intended to limit the scope of the invention.

EXAMPLE 1

A mixture of 5 g of a fine powder of glucose, 5 g of palladium-activated carbon (5% palladium carried) available from Engelhard Minerals & Chemicals Corp. and 260 g of methanol was charged into a 500 cc flask and stirred for reaction at 40° C. for a period of 1.5 hours, during which oxygen was supplied to the mixture via a filter-equipped inlet tube. After the reaction, the catalyst was filtered off, and the content of glucono-delta-lactone in the filtrate was determined by gas chromatography under the following conditions:
Adsorbent: OV-17 (Shimalite W available from Shimazu Seisakusho, Ltd.)
Column height: 2 m
Column temperature: 180° C.
Injection temperature: 220° C.

The amount of the unreacted glucose was determined by high performance liquid chromatography under the following condition:
Adsorbent: Microbondapack CH
Solvent: water:acetonitrile=15:85 (volume ratio)
Solvent flow rate: 1 ml/min
The following results were obtained.
Glucose conversion ratio: 62%
Yield of glucono-delta-lactone: 48%

EXAMPLE 2

A mixture of 5 g of glucose, 5 g of palladium-silica (5% palladium carried) and 100 g of N.methylpyrrolidone was charged into a 200 cc flask and stirred for reaction at 100° C. for a period of 40 minutes with oxygen supplied continuously. After the reaction, the catalyst was filtered off, and the contents of the unreacted glucose and the resulting glucono-delta-lactone in the filtrate were determined as in Example 1.
Glucose conversion ratio: 47%
Yield of glucono-delta-lactone: 39%

EXAMPLE 3

A mixture of 5 g of glucose, 5 g of palladium-activated carbon (5% palladium carried) and 200 g of dimethoxyethane was charged into a 500 cc flask and stirred for reaction at 70° C. for a period of one hour with oxygen supplied continuously. After the reaction, the catalyst was filtered off, and the contents of the unreacted glucose and the resulting glucono-delta-lactone in the filtrate were determined as in Example 1.
Glucose conversion ratio: 42%
Yield of glucono-delta-lactone: 37%

EXAMPLE 4

A mixture of 5 g of glucose, 5 g of palladium-alumina (5% palladium carried), 200 g of dioxane and 1 g of water was charged into a 500 cc flask and stirred for reaction at 50° C. for a period of one hour with oxygen supplied continuously. After the reaction, the catalyst was filtered off, and the contents of the unreacted glucose and the resulting glucono-delta-lactone in the filtrate were determined as in Example 1.
Glucose conversion ratio: 40%
Yield of glucono-delta-lactone: 32%

EXAMPLE 5

A mixture of 5 g of glucose, 10 g of palladium-activated carbon (5% palladium carried), 100 g of methanol and 1 g of water charged into a 200 cc flask and subjected to reaction under the same conditions as Example 1. After the reaction, the catalyst was filtered off, and the contents of the unreacted glucose and the resulting glucono-delta-lactone in the filtrate were determined as in Example 1.
Glucose conversion ratio: 60%
Yield of glucono-delta-lactone: 47%

EXAMPLE 6

A mixture of 5 g of glucose, 7 g of palladium-barium carbonate (3% palladium carried), 200 g of methyl acetate and 0.5 g of water was charged into a 200 cc flask and subjected to reaction under the same conditions as Example 1. After the reaction, the catalyst was filtered off, and the contents of the unreacted glucose and the resulting glucono-delta-lactone in the filtrate were determined as in Example 1.
Glucose conversion ratio: 38%
Yield of glucono-delta-lactone: 33%

EXAMPLE 7

A mixture of 5 g of a fine powder of glucose, 10 g of palladium-alumina (3% palladium carried) and 200 g of n-butanol was subjected to reaction under the same conditions as Example 1. After the reaction, the catalyst was filtered off, and the contents of the unreacted glucose and the resulting glucono-delta-lactone in the filtrate were determined as in Example 1.
Glucose conversion ratio: 40%
Yield of glucono-delta-lactone: 31%

EXAMPLE 8

A mixture of 5 g of a fine powder of glucose, 5 g of palladium-activated carbon (3% palladium carried) and 150 g of diethylene glycol dimethyl ether was subjected to reaction under the same conditions as Example 1. After the reaction, the catalyst was filtered off, and the contents of the unreacted glucose and the resulting glucono-delta-lactone in the filtrate were determined as in Example 1.
  Glucose conversion ratio: 43%
  Yield of glucono-delta-lactone: 34%

EXAMPLE 9

A mixture of 5 g of a fine powder of glucose, 7 g of granular platinum-aluminum (5% platinum carried), and 100 g of methanol was charged into a 200 cc flask and stirred for reaction at 30° C. for a period of one hour during which oxygen was supplied to the reaction mixture through a filter-equipped inlet tube. After the reaction, the catalyst was filtered off, and the contents of the unreacted glucose and the resulting glucono-delta-lactone in the filtrate were determined by high performance liquid chromatography.
  Glucose conversion ratio: 62%
  Yield of glucono-delta-lactone: 49%

EXAMPLE 10

A mixture of 5 g of glucose, 10 g of platinum-silica (2% platinum carried) and 70 g of dimethylformamide was charged into a 200 cc flask and stirred for reaction at 60° C. for a period of one hour, during which oxygen was supplied to the reaction mixture through a filter-equipped inlet tube. After the reaction, the catalyst was filtered off, and the contents of the unreacted glucose and the resulting glucono-delta-lactone in the filtrate were determined as in Example 1.
  Glucose conversion ratio: 47%
  Yield of glucono-delta-lactone: 33%

EXAMPLE 11

A mixture of 5 g of glucose, 5 g of platinum-silica-alumina (10% platinum carried) and 100 g of tetramethylurea was charged into a 200 cc flask and stirred for reaction at 100° C. for a period of one hour during which oxygen was supplied to the reaction mixture through a filter-equipped tube. After the reaction, the catalyst was filtered off, and the contents of the unreacted glucose and the resulting glucono-delta-lactone in the filtrate was determined as in Example 1.
  Glucose conversion ratio: 48%
  Yield of glucono-delta-lactone: 36%

EXAMPLE 12

A mixture of 5 g of glucose, 10 g of platinum-silica (1% platinum carried) and 100 g of triethylene glycol dimethyl ether was charged into a 200 cc flask and stirred for reaction at 50° C. for a period of 2 hours during which air was supplied to the reaction mixture through a filter-equipped tube. After the reaction, the catalyst was filtered off, and the contents of the unreacted glucose and the resulting glucono-delta-lactone in the filtrate were determined as in Example 1.
  Glucose conversion ratio: 55%
  Yield of glucono-delta-lactone: 44%

EXAMPLE 13

A mixture of 5 g of glucose, 5 g of platinum-calcium carbonate (2% platinum carried) and 100 g of dioxane was charged into a 200 cc flask and stirred for reaction at 75° C. for a period of 2 hours during which air was supplied to the reaction mixture through a filter-equipped tube. After the reaction, the catalyst was filtered off, and the contents of the unreacted glucose and the resulting glucono-delta-lactone in the filtrate were determined as in Example 1.
  Glucose conversion ratio: 56%
  Yield of glucono-delta-lactone: 45%

EXAMPLE 14

A mixture of 5 g of a fine powder of glucose, 5 g of platinum-barium sulfate (5% platinum carried) and 150 g of n-butyl acetate was charged into a 200 cc flask and subjected to reaction at 80° C. for a period of 2 hours during which air was supplied to the reaction mixture through a filter-equipped tube. After the reaction, the catalyst was filtered off, and the contents of the unreacted glucose and the resulting glucono-delta-lactone in the filtrate were determined as in Example 1.
  Glucose conversion ratio: 38%
  Yield of glucono-delta-lactone: 32%

EXAMPLE 15

A mixture of 5 g of a fine powder of glucose, 10 g of platinum-calcium phosphate (5% platinum carried) and 100 g of n-butanol was charged into a 200 cc flask and subjected to reaction at 110° C. for a period of 0.5 hour, during which oxygen was supplied to the reaction mixture through a filter-equipped tube. After the reaction, the catalyst was filtered off, and the contents of the unreacted glucose and the resulting glucono-delta-lactone in the filtrate were determined as in Example 1.
  Glucose conversion ratio: 59%
  Yield of glucono-delta-lactone: 43%

EXAMPLE 16

A mixture of 5 g of a fine powder of glucose, 3 g of platinum-alumina (10% platinum carried) and 100 g of diethyl ether was charged into a 200 cc flask and subjected to reaction at 25° C. for a period of 7 hours during which oxygen was supplied to the reaction mixture through a filter-equipped tube. After the reaction, the catalyst was filtered off, and the contents of the unreacted glucose and the resulting glucono-delta-lactone in the filtrate were determined as in Example 1.
  Glucose conversion ratio: 23%
  Yield of glucono-delta-lactone: 20%

EXAMPLE 17

A mixture of 5 g of glucose, 3 g of platinum-activated carbon (10% platinum carried), 100 g of dioxane and 3 g of water was charged into a 200 cc flask and subjected to reaction under stirring at 60° C. for a period of 2 hours with oxygen being supplied continuously. After the reaction, the catalyst was filtered off, and the contents of the unreacted glucose and the resulting glucono-delta-lactone in the filtrate were determined as in Example 1.
  Glucose conversion ratio: 77%
  Yield of glucono-delta-lactone: 55%

EXAMPLE 18

A mixture of 5 g of glucose, 6 g of platinum-alumina (3% platinum carried), 100 g of 1,2-dimethoxyethane and 20 g of methanol was charged into a 300 cc flask and subjected to reaction under stirring at 50° C. for a period of 3 hours with oxygen being supplied continuously. After the reaction, the catalyst was filtered off, and the contents of the unreacted glucose and the resulting glucono-delta-lactone in the filtrate were determined as in Example 1.
  Glucose conversion ratio: 59%

Yield of glucono-delta-lactone: 47%

EXAMPLE 19

A mixture of 5 g of glucose, 5 g of platinum-silica-alumina (10% platinum carried), 50 g of diemthylformamide and 20 g of methanol was charged into a 200 cc flask and subjected to reaction under stirring at 50° C. for a period of 3 hours with oxygen being supplied continuously. After the reaction, the catalyst was filtered off, and the contents of the unreacted glucose and the resulting glucono-delta-lactone in the filtrate were determined as in Example 1.

Glucose conversion ratio: 40%
Yield of glucono-delta-lactone: 29%

EXAMPLE 20

A mixture of 5 g of a fine powder of glucose, 5 g of a catalyst on activated carbon (5% palladium carried, Pd:Pb=1:2 (atomic ratio), Pb as PbO) and 100 g of 1,2-dimethoxyethane was charged into a 200 cc flask and subjected to reaction under stirring at 70° C. for a period of one hour during which 50 cc/min of oxygen was supplied to the reaction mixture through a filter-equipped tube. After the reaction, the catalyst was filtered while hot, the filtrate concentrated and the contents of the unreacted glucose and the resulting glucono-delta-lactone was determined by high performance liquid chromatography under the following conditions:
Adsorbent: Microbondapack CH
Solvent: Water: acetonitrile = 1:99 (volume ratio)
Solvent flow rate: 2 ml/min
Glucose conversion ratio: 87%
Yield of glucono-delta-lactone: 83%
Selectivity of glucono-delta-lactone: 95%

The catalyst was filtered off while the reaction mixture was hot, and the filtrate was concentrated and left to stand overnight to give 29 g of glucono-delta-lactone.

EXAMPLE 21

A mixture of 5 g of a fine powder of glucose, 5 g of silica-carried catalyst (3% palladium carried, Pd:Pb=1:4 (atomic ratio), Pb as PbO) and 150 g of dioxane was charged into a 300 cc flask and subjected to reaction under stirring at 50° C. for a period of 1.5 hours during which 50 cc/min of oxygen was supplied to the reaction mixture through a filter-equipped tube. After the reaction, the catalyst was filtered off while the reaction mixture was hot, and the contents of the unreacted glucose and the resulting glucono-delta-lactone were determined by high performance liquid chromatography as in Example 20.

Glucose conversion ratio: 78%
Yield of glucono-delta-lactone: 74%
Selectivity of glucono-delta-lactone: 95%

EXAMPLE 22

A mixture of 5 g of glucose, 5 g of a catalyst on activated carbon (5% palladium carried, Pd:Pb=1:2 (atomic ratio), Pb as PbO) and 150 g of a solvent selected from the solvent list given below was charged into a 300 cc flask and subjected to reaction under stirring at 60° C. for a period of 2 hours during which oxygen was supplied to the reaction mixture at a rate of 50 cc/min through a filter-equipped tube. After the reaction, the catalyst was filtered while hot, the filtrate concetrated and the contents of the unreacted glucose and the resulting glucono-delta-lactone was determined by high performance liquid chromatography as in Example 20. The results of the reaction are set forth in the list below.

| Solvent | Glucose Conversion Ratio (%) | Glucono-delta-lactone Yield (%) | Glucono-delta-lactone Selectivity (%) |
|---|---|---|---|
| Diisopropyl ether | 82 | 79 | 96 |
| Tetrahydrofuran | 80 | 74 | 93 |
| Acetonitrile | 41 | 39 | 95 |
| Propionitrile | 43 | 39 | 90 |
| Dimethylformamide | 83 | 53 | 61 |
| Ethyl acetate | 42 | 34 | 81 |
| Methyl ethyl ketone | 54 | 51 | 94 |
| Nitromethane | 67 | 48 | 72 |
| Pyridine | 83 | 58 | 70 |
| Cyclohexane | 42 | 40 | 96 |

EXAMPLE 23

A mixture of 5 g of glucose, 10 g of a catalyst on silica-alumina (5% palladium carried, Pd:Pb=1:10 (atomic ratio), Pb as $Pb(OAl)_2$) and 150 g of 1,2-dimethoxyethane was charged into a 300 cc flask and subjected to reaction under the same conditions as Example 20. After the reaction, the catalyst was filtered while hot, the filtrate concentrated and the contents of the unreacted glucose and the resulting glucono-delta-lactone were determined by high performance liquid chromatography as in Example 20.

Glucose conversion ratio: 67%
Yield of glucono-delta-lactone: 63%
Selectivity of glucono-delta-lactone: 94%

EXAMPLE 24

A mixture of 5 g of glucose, 5 g of a catalyst on activated carbon (5% palladium carried, Pd:Pb=1:1 (atomic ratio), Pb as $Pb(OOC-CH_2CH_3)_2$) and 150 g of benzonitrile was charged into a 300 cc flask and subjected to reaction under the same conditions as Example 20. After the reaction, the catalyst was filtered while hot, the filtrate concentrated and the contents of the unreacted glucose and the resulting glucono-delta-lactone were determined by high performance liquid chromatography as in Example 20.

Glucose conversion ratio: 53%
Yield of glucono-delta-lactone: 48%
Selectivity of glucono-delta-lactone: 91%

EXAMPLE 25

A mixture of 5 g of glucose, 5 g of a catalyst on activated carbon (5% palladium carried, Pd:Pb=1:5 (atomic ratio), Pb as $Pb(OH)_2$) and 100 g of trichloroethylene was charged into a 200 cc flask and subjected to reaction under the same conditions as Example 20. After the reaction, the catalyst was filtered while hot, the filtrate concentrated and the contents of the unreacted glucose and the resulting glucono-delta-lactone were determined by high performance liquid chromatography as in Example 20.

Glucose conversion ratio: 37%
Yield of glucono-delta-lactone: 33%
Selectivity of glucono-delta-lactone: 89%

EXAMPLE 26

A mixture of 5 g of glucose, 5 g of a silica-carried catalyst (5% palladium carried, Pd:Pb=1:2 (atomic ratio), Pb as metallic lead) and 100 g of methanol was charged into a 200 cc flask and subjected to reaction at 20° C. for a period of 2 hours during which air was supplied at a rate of 50 cc/min. After the reaction, the catalyst was filtered while hot, the filtrate concentrated and the contents of the unreacted glucose and the resulting glucono-delta-lactone were determined by high performance liquid chromatography as in Example 20.
Glucose conversion ratio: 64%
Yield of glucono-delta-lactone: 46%
Selectivity of glucono-delta-lactone: 72%

EXAMPLE 27

A mixture of 5 g of glucose, 10 g of alumina-carried catalyst (5% palladium carried, Pd:Pb=1:0.5 (atomic ratio), Pb as Pb(NO$_3$)$_2$) and 100 g of dioxane was charged into a 300 cc flask and subjected to reaction at 70° C. for a period of 2 hours with air supplied continuously. After the reaction, the catalyst was filtered while hot, the filtrate concentrated and the contents of the unreacted glucose and the resulting glucono-delta-lactone were determined by high performance liquid chromatography as in Example 20.
Glucose conversion ratio: 62%
Yield of glucono-delta-lactone: 39%
Selectivity of glucono-delta-lactone: 63%

EXAMPLE 28

A mixture of 5 g of glucose, 5 g of a catalyst on activated carbon (5% palladium carried, Pd:Pb=1:3 (atomic ratio), Pb as PbBr$_2$) and 70 g of n-butanol was charged into a 200 cc flask and subjected to reaction under the same conditions as Example 20. After the reaction, the catalyst was filtered while hot, the filtrate concentrated and the contents of the unreacted glucose and the resulting glucono-delta-lactone were determined by high performance liquid chromatography as in Example 20.
Glucose conversion ratio: 50%
Yield of glucono-delta-lactone: 41%
Selectivity of glucono-delta-lactone: 82%

EXAMPLE 29

A mixture of 5 g of glucose, 5 g of a catalyst on activated carbon (5% palladium, Pb absent), 0.1 g of lead acetate, and 100 g of 1,2-dimethoxyethane was charged into a 200 cc flask and subjected to reaction under stirring at 70° C. for a period of 1.5 hours, during which oxygen was supplied to the reaction mixture at a rate of 50 cc/min through a filter-equipped tube. After the reaction, the catalyst was filtered off while hot, and the filtrate was analyzed for the contents of the unreacted glucose and the resulting glucono-delta-lactone as in Example 20.
Glucose conversion ratio: 69%
Yield of glucono-delta-lactone: 63%
Selectivity of glucono-delta-lactone: 91%

EXAMPLE 30

A mixtuure of 5 g of a fine powder of glucose, 5 g of a silica-carried catalyst (5% palladium carried, Pd:Pb=1:2 (atomic ratio), Pb as PbO) and 100 g of dioxane was charged into a 200 cc flask and subjected to reaction under stirring at 70° C. for a period of 2 hours, during which 50 cc/min of oxygen was supplied to the reaction mixture through a filter-equipped tube. After the reaction, the catalyst was filtered off while hot, and the filtrate was mixed with 2 g of an ion exchange resin ("Amberlist 15" available from Rohm & Haas) under stirring at 20° C. for a period of 30 minutes. After filtration of the ion exchange resin, the filtrate was concentrated, and the contents of the unreacted glucose and the resulting glucono-delta-lactone were determined by high performance liquid chromatography under the following conditions.
Adsorbent: Shodex IONPAK S-801 (a product of Showa Denko K.K.)
Solvent: Water
Solvent flow rate: 2 ml/min
Glucose conversion ratio: 88% (87%)*
Yield of glucono-delta-lactone: 83% (67%)*
Selectivity of glucono-delta-lactone: 94% (77%)*
* The values in parentheses were obtained when the reaction mixture was not treated with an in exchange resin.

EXAMPLE 31

A mixture of 5 g of a fine powder of glucose, 10 g of a catalyst on activated carbon (5% palladium carried), and 200 g of dimethoxyethane was charged into a 300 cc flask and subjected to reaction under stirring at 70° C. for a period of 5 hours, during which oxygen was supplied to the reaction mixture through a filter-equipped tube at a rate of 50 cc/min. After the reaction, the catalyst was filtered off while hot, the solent was distilled off, the crude product was dissolved in 30 ml of methanol, and mixed with 0.1 cc of concentrated hydrochloric acid under stirring at 20° C. for a period of 10 minutes. The methanol solution was analyzed for the contents of the unreacted glucose and the resulting glucono-delta-lactone by liquid chromatography as in Example 30.
Glucose conversion ratio: 67%
Yield of glucono-delta-lactone: 60%
Selectivity of glucono-delta-lactone: 90%

EXAMPLE 32

A mixture of 5 g of a fine powder of glucose, 10 g of alumina-carried catalyst (5% platinum carried) and 70 g of dimethylformamide was charged into a 200 cc flask and subjected to reaction under stirring at 60° C. for a period of 2 hours, during which 70 cc/min of oxygen was supplied to the reaction mixture through a filter-equipped inlet tube. After the reaction, the catalyst was filtered off, and dimethylformamide was distilled off the filtrate. Thereafter, the reaction product was dissolved in 30 ml of methanol and mixed with 0.2 g of paratoluenesulfonic acid under stirring at 40° C. for a period of 10 minutes. The methanol solution was analyzed for the contents of the unreacted glucose and the resulting glucono-delta-lactone by liquid chromatography as in Example 30.
Glucose conversion ratio: 66% (66%)*
Yield of glucono-delta-lactone: 57% (41%)*
Selectivity of glucono-delta-lactone: 86% (62%)*
* The values in parentheses were obtained when the reaction mixture was not treated with paratoluenesulfonic acid.

EXAMPLE 33

A mixture of 5 g of glucose, 10 g of a catalyst on activated carbon (5% palladium carried, Pd:Pb=1:0.8 (atomic ratio), Pb as lead acetate) and 200 g of acetonitrile was charged into a 300 cc flask and subjected to reaction under stirring at 50° C. for a period of 4 horus, during which air was supplied at a rate of 100 cc/min. After the reaction, the catalyst was filtered off while hot and the filtrate was mixed with 3 g of an ion exchange resin ("Amberlist 15" available from Rohm & Haas) under heating at 20° C. for a period of 20 minutes.

After filtering the ion exchange resin off, the filtrate was analyzed for the contents of the unreacted glucose and the resulting glucono-delta-lactone as in Example 30.

Glucose conversion ratio: 59% (59%)*
Yield of glucono-delta-lactone: 54% (41%)*
Selectivity of glucono-delta-lactone: 92% (70%)*

* The values in parentheses were obtained when the reaction mixture was not treated with an ion exchange resin.

While the invention has been described in detail and with reference to specific embodiments thereof, it will be apparent to one skilled in the art that various changes and modifications can be made therein without departing from the spirit and scope thereof.

What is claimed is:

1. A process for producing glucono-delta-lactone from glucose using an organic solvent by bringing glucose into contact with molecular oxygen in the presence of a palladium or platinum catalyst, wherein the organic solvent is selected from the group consisting of an ether, a nitrile, an alcohol, an amide, an ester, a ketone, a nitro compound, a pyridine base, a hydrocarbon and a halogenated hydrocarbon.

2. The process of claim 1, wherein the palladium catalyst contains lead.

3. The process of claim 2, wherein the lead is present in the form of metallic lead or a lead compound.

4. The process of claim 3, wherein the lead compound is a hydroxide, inorganic acid salt or organic acid salt of lead.

5. The process of claim 2, wherein the lead is present in an amount 0.01 to 30 times the amount of palladium in terms of atomic ratio.

6. The process of claim 1, wherein the reaction is performed at a temperature in the range of from 10° to 200° C.

7. A process of producing glucono-delta-lactone from glucose using an organic solvent wherein glucose is contacted with molecular oxygen in the presence of a palladium or platinum catalyst, filtering the catalyst from the reaction mixture, and treating the filtrate or the crude product with an acid, wherein the organic solvent is selected from the group consisting of an ether, a nitrile, an alcohol, an amide, an ester, a ketone, a nitro compound, a pyridine base, a hydrocarbon and a halogenated hydrocarbon.

8. The process of claim 7, wherein the acid is an inorganic acid, an organic acid or an acidic ion exchange resin.

9. The process of claim 8, wherein the acid is used in an amount of from about 0.001 to 0.1 mol per mol of glucose.

10. The process of claims 1 or 7, wherein said palladium or platinum is present in an amount of about 0.001 to 1 atom per mol of glucose.

11. The process of claim 1, wherein said palladium or platinum catalyst is a supported catalyst.

12. The process of claim 2, wherein said palladium catalyst contains lead and is a supported catalyst.

13. The process of claims 11 or 12, wherein said supported catalyst carrier is activated carbon, silica, silica-alumina, alumina, calcium carbonate, calcium sulfate, barium sulfate or alumina-magnesia.

14. The process of claim 7, wherein said acid treatment is carried out at a temperature of about 10° to 70° C.

15. The process of claim 1 or 7, wherein said organic solvent is selected from the group consisting of dioxane, tetrahydrofuran, dimethoxyethane, diisopropyl ether, dibutyl ether, diethylene glycol dimethyl ether, triethylene glycol dimethyl ether, methanol, n-butanol, dimethylformamide, dimethylacetamide, tetramethylurea, methyl acetate and ethyl acetate.

16. The process of claim 1 or 7, wherein the organic solvent is diethyl ether, diisopropyl ether, dibutyl ether, phenylethyl ether, anisole, dimethoxyethane, diethylene glycol dimethyl ether, diethylene glycol diethyl ether, acetic ethylene glycol monomethyl ether, triethylene glycol dimethyl ether, ethylene glycol monoethyl ether, tetrahydrofuran, dioxane, acetonitrile, propionitrile, n-butyronitrile, ethylene cyanohydrin, benzonitrile, methanol, ethanol, propanol, n-butanol, amyl alcohol, dimethylformamide, dimethylacetamide, N-methylpyrrolidone, tetramethylurea, hexamethyl phosphoryl amide, methyl formate, ethyl formate, methyl acetate, ethyl acetate, propyl acetate, butyl acetate, benzyl acetate, methyl acetoacetate, ethyl acetoacetate, glycol diacetate, acetone, methyl ethyl ketone, methyl propyl ketone, methyl butyl ketone, methyl isobutyl ketone, dipropyl ketone, nitromethane, nitroethane, trinitropropane, nitrobenzene, pyridine, α-methylpyridine, β-methylpyridine, γ-methylpyridine, n-pentane, n-hexane, heptane, cyclohexane, methylcyclohexane benzene, toluene, xylene, ethylbenzene, diethylbenzene, triethylbenzene, chloroform, methylchloroform, 1,1,2-trichloroethane, 1,2,3-trichloroethane, trichloroethylene, ethylene chlorohydrin, ethylene dichloride, ethylene dibromide, chlorobenzene, dichlorobenzene or monochlorotoluene.

17. The process of claim 7, wherein the palladium catalyst contains lead.

18. The process of claim 8, wherein the acid is hydrochloric acid, sulfuric acid, nitric acid, phosphoric acid, boric acid, paratoluenesulfonic acid or an acidic ion exchange resin.

* * * * *